(12) United States Patent
Pirsch et al.

(10) Patent No.: US 7,765,868 B2
(45) Date of Patent: Aug. 3, 2010

(54) CLIMATE CHAMBER FOR MICROSCOPES

(75) Inventors: Matthias Pirsch, Hamburg (DE); Stefan Hummel, Haseldorf (DE)

(73) Assignee: Evotec Technologies GmbH (DE)

( * ) Notice: Subject to any disclaimer, the term of this patent is extended or adjusted under 35 U.S.C. 154(b) by 248 days.

(21) Appl. No.: 10/571,297

(22) PCT Filed: Sep. 20, 2004

(86) PCT No.: PCT/EP2004/010531

§ 371 (c)(1),
(2), (4) Date: Feb. 15, 2007

(87) PCT Pub. No.: WO2005/030394

PCT Pub. Date: Apr. 7, 2005

(65) Prior Publication Data

US 2007/0234829 A1    Oct. 11, 2007

(30) Foreign Application Priority Data

Sep. 23, 2003 (DE) ................. 103 44 294
Sep. 23, 2003 (DE) ................. 103 44 295

(51) Int. Cl.
*G01N 21/01* (2006.01)
*G01D 11/24* (2006.01)
(52) U.S. Cl. ............... 73/431; 73/865.6; 359/398
(58) Field of Classification Search ............ 73/431, 73/865.6, 865.5; 359/368–398
See application file for complete search history.

(56) References Cited

U.S. PATENT DOCUMENTS

| | | | | |
|---|---|---|---|---|
| 3,393,032 A * | 7/1968 | Crisler et al. | ............... | 359/513 |
| 3,907,389 A * | 9/1975 | Cox et al. | ............... | 312/1 |
| 3,984,678 A * | 10/1976 | Uchiyama et al. | ............... | 250/231.1 |
| 4,301,252 A * | 11/1981 | Baker et al. | ............... | 435/303.1 |
| 4,405,202 A * | 9/1983 | Kimball | ............... | 359/513 |
| 4,589,742 A * | 5/1986 | Schindl | ............... | 359/513 |
| 4,627,287 A * | 12/1986 | Suga | ............... | 73/865.6 |
| 4,629,862 A * | 12/1986 | Kitagawa et al. | ............... | 219/200 |
| 4,667,522 A * | 5/1987 | Kawahara | ............... | 73/865.6 |
| 4,696,902 A | 9/1987 | Bisconte | ............... | 435/286.2 |
| 4,705,366 A * | 11/1987 | Kimura et al. | ............... | 359/391 |
| 4,817,447 A * | 4/1989 | Kashima et al. | ............... | 73/865.6 |
| 4,843,893 A * | 7/1989 | Huber et al. | ............... | 73/865.6 |
| 4,855,601 A * | 8/1989 | Savoyet | ............... | 250/339.12 |
| 4,892,830 A * | 1/1990 | Findley et al. | ............... | 435/286.6 |
| 4,931,655 A * | 6/1990 | Yoshida et al. | ............... | 250/492.1 |
| 5,138,892 A * | 8/1992 | Suga | ............... | 73/865.6 |
| 5,233,203 A * | 8/1993 | Haga | ............... | 250/559.41 |

(Continued)

FOREIGN PATENT DOCUMENTS

DE        36 07 575 A        9/1987

(Continued)

*Primary Examiner*—David A. Rogers
(74) *Attorney, Agent, or Firm*—Ohlandt, Greeley, Ruggiero & Perle, LLP

(57) ABSTRACT

A climate chamber, which is in particular suitable for chemical and/or biological samples, comprises a climate compartment defined by a housing. Inside the climate compartment an analysis device, such as a microscope, is at least partially arranged. Further, the housing comprises an inlet opening for supplying a conditioning medium flow. For preventing condensation at condensate-sensitive components the medium flow is directed such that it at least partially flows against the analysis device and/or the sample carrier.

19 Claims, 2 Drawing Sheets

U.S. PATENT DOCUMENTS

| | | | | |
|---|---|---|---|---|
| 5,285,672 | A * | 2/1994 | Yao | 73/1.04 |
| 5,503,032 | A * | 4/1996 | Tikhtman et al. | 73/865.6 |
| 5,618,446 | A * | 4/1997 | Nagaishi | 216/65 |
| 5,654,200 | A * | 8/1997 | Copeland et al. | 436/46 |
| 6,051,825 | A * | 4/2000 | Lindsay et al. | 250/201.3 |
| 6,241,650 | B1 * | 6/2001 | Letourneur | 494/11 |
| 6,318,864 | B1 * | 11/2001 | Fukaya et al. | 359/510 |
| 6,490,913 | B1 * | 12/2002 | Martin et al. | 73/105 |
| 6,590,212 | B1 * | 7/2003 | Joseph et al. | 250/311 |
| 6,674,077 | B1 * | 1/2004 | Joseph et al. | 250/311 |
| 6,711,961 | B2 * | 3/2004 | Theriault et al. | 73/865.6 |
| 2002/0196421 | A1 * | 12/2002 | Tanaka et al. | 355/72 |
| 2005/0146708 | A1 * | 7/2005 | Shi et al. | 356/35.5 |
| 2007/0177258 | A1 * | 8/2007 | Eijsackers et al. | 359/393 |

FOREIGN PATENT DOCUMENTS

| | | | |
|---|---|---|---|
| JP | 09021960 A | * | 1/1997 |
| JP | 2003 107364 A | | 4/2003 |

* cited by examiner

CLIMATE CHAMBER FOR MICROSCOPES

FIELD OF THE INVENTION

The invention relates to a climate chamber which is in particular suitable for chemical and/or biological samples.

DISCUSSION OF THE BACKGROUND ART

In the case of chemical and/or biological samples, such as cells, it is necessary, for example for analyzing the cell growth or other reactions, to expose the sample to a defined climate over a longer period. With regard to the climate, in particular the temperature and the moisture content in a climate compartment, where the sample is arranged, are of great importance. Further, gas constituents, such as the quantity of $CO_2$ etc., may be relevant.

From JP 2003107364 a climate chamber is known in which a sample carrier is arranged. The defined climate compartment exclusively encloses the sample carrier and comprises a transparent cover which allows the sample to be analyzed or observed with the aid of an analysis device, such as a microscope. Provision of such a climate chamber has the drawback that the analysis device must be arranged at a relatively large distance to the sample. Further, the sample is observed through a transparent cover such that refractions and the like may falsify optical signals.

It is an object of the invention to provide a climate chamber which offers improved possibilities for analyzing a sample.

SUMMARY OF THE INVENTION

According to the invention, a climate compartment, which is defined by a housing, of the climate chamber at least partially encloses an analysis device, such as a microscope or the like. Thus, in particular the essential components of an analysis device, for example the optical and illumination means of a microscope, are arranged inside the climate compartment. In particular the optical means or any other portion of the analysis device can thus be guided to a location very near the sample to be analyzed, without necessitating an outer wall or a cover of a climate chamber to be arranged between the sample and the analysis device, which outer wall or cover may falsify the measuring results.

Further, the climate chamber according to the invention comprises an inlet opening through which a conditioning medium flow can be introduced into the climate chamber. In particular air with, for example, a defined air moisture and/or temperature is introduced. If necessary, gases contained in the air, such as $CO_2$, can be defined. Since the medium flow can in particular have a relatively high air moisture for increasing the air moisture in the climate compartment, there is the risk of condensation at cold components, such as the sample carrier and in particular portions of the analysis device. Since condensation at such components may lead to a considerable falsification of the analysis results, the invention provides for the medium flow to be introduced into the climate compartment such that at least a portion of the medium flow flows against the analysis device and/or the sample carrier. Preferably, the flow flows against both the sample carrier and the critical components of the analysis device. Thus, condensation in this region is prevented.

Preferably, the climate chamber comprises a directing means for directing the medium flow to the corresponding portions of the analysis device and/or the sample carrier. The directing means may be a sidewall of the housing, which side wall comprises the inlet opening and is arranged at a specific angle to the portions to which the flow is directed. The angle is dependent on the design of the microscope. Preferably, the approach flow angle relative to the sample carrier, preferably relative to a lower side of the sample carrier, is 30°-60°, preferably 40°-50°. In the case of a sample carrier arranged horizontally in the climate compartment, said sample carrier preferably being a microtiter plate, the flow approaches the sample carrier from below. Preferably, the directing means is adapted to be displaced and/or adjusted. This can be realized by providing a separate directing means. It is further possible to change the position of a flexible supply line, which supplies the medium flow to the climate compartment, relative to the inlet opening, thus adjusting the approach flow angle. Further, flow guide elements or plates and the like may be provided.

Preferably, the medium flow is directed such that 50%-70% of the medium flow flows against the corresponding parts, i.e. in particular the optical means of the analysis device and the sample carrier. This advantageously allows condensate-sensitive components, such as the lenses and the illumination means of the sample carrier, to be heated and thus condensation of moisture to be prevented, and, additionally, the climate compartment to be uniformly heated.

Further, a temperature sensor is preferably arranged near the sample carrier. With the aid of a corresponding control means the temperature near the sample carrier can thus be very precisely adjusted. Further, a moisture sensor, a gas sensor etc. can preferably also be provided near the sample carrier. In a particularly preferred variant, the sensors, in particular the temperature sensor, are arranged below the sample carrier. This is of advantage in particular with titer plates, since this allows the temperature near the titer plate bottom and thus the approximate temperature of the titer plate bottom itself to be determined. The sample comes into direct contact with the bottom such that the approximate temperature of the sample can be determined by arranging the temperature sensor near and below the sample carrier. Determination of the temperature with such an exactness would not be possible if the temperature sensor were arranged above the sample carrier, since, for example, an air cushion exists between a cover of the sample carrier and the sample, said air cushion affecting the heat transfer between the sample carrier and the sample.

In a particularly preferred embodiment, the housing is configured such that it promotes an optimum flow. Consequently, only a very small quantity of condensate is found at the housing inner wall. Flow optimization can preferably be realized by arranging two adjacent walls at an angle of at least 90° relative to each other. Preferably, the housing walls are arranged at an angle of more than 90°, in particular more than 120°, relative to each other. In such a configuration the medium flow flows against the interior of the housing, and there are hardly any "dead nooks".

Preferably, the chamber wall of the climate chamber according to the invention comprises one or a plurality of openings through which manipulators, for example robot arms, can be inserted into the interior of the climate chamber. Preferably, collar seals or other seals for sealing the opening are provided between the manipulators and the chamber wall. When the manipulators are not or no longer required, they can be removed or withdrawn from the chamber through the openings. The openings can then be closed, for example with a screw cap or any other closing element. Preferably, only the manipulators, i.e. for example the robot arms, are inserted through the openings into the chamber. Operating elements, motor drives and the like of the manipulators are preferably arranged outside the chamber.

In a particularly preferred embodiment of the invention, a redirecting element for redirecting the medium flow is arranged in the region where the sample carrier, an object carrier or the like is disposed. In this manner, it can be ensured, for example in the case of a relatively dry medium flow, that the rate of evaporation of a liquid sample is as small as possible.

For simple observation of the sample, for example during operation of the manipulators, or other kinds of observation, the chamber wall of the climate chamber is at least partially transparent. Further, the chamber wall may comprise windows which allow observation of the sample etc. The windows or the transparent portions of the chamber wall can preferably be shaded or closed. This can be of advantage, for example, when analyzing light-sensitive samples.

The temperature of a sample or an object to be analyzed, which is arranged in the climate chamber, may be adjusted to the desired value exclusively by supplying a medium flow of the desired temperature into the climate chamber. This applies as well to the surroundings of the sample or the object, or to the overall climate chamber. In addition to or instead of heating the sample with the aid of the medium flow, heating can also be effected by providing heating elements. Said heating elements may, for example, be electric heating elements arranged directly in the climate chamber, but also radiators which may be arranged outside the climate chamber, if necessary. Heating can thus be effected by convection and/or radiation.

In a particularly preferred variant, the housing additionally comprises an outlet opening which allows the inflowing medium to leave the climate compartment not only as leakage medium. This offers the advantage that the quantity of medium supplied can be very high without pressure being built up in the climate compartment. Preferably, the outlet opening has connected therewith a discharge channel, such as a flexible tube or the like. Said channel preferably extends to a climate generation or control device such that the medium flow is pumped in a closed circuit. With the aid of the climate control device, for example, steam for increasing the air moisture is produced and/or the medium flow is heated and/or gases are introduced. The invention thus relates to a climate control means comprising a climate chamber and a climate control device.

Such a climate generation device, in particular a climate control device, is an independent invention. Preferably, according to the invention, the climate control device is connected with the climate chamber.

It is common practice to expose chemical and/or biological samples, such as cells, over a longer period to a defined climate in climate control devices, in particular in incubators. In this connection it is in particular necessary to maintain the air moisture and the temperature within a predetermined range. Further, the atmosphere, for example the $CO_2$ content in the incubator, is of importance. For controlling the moisture, in particular the air moisture, in an incubator, it is common practice to sprinkle a sponge with water and pass warm air through the sponge. However, such a moisture control has the drawback that the period from introducing the sample into the climate chamber to reaching the desired moisture value is relatively large. At a required moisture value of 80% and a chamber volume of 50-70 liters said period lies in the range of approximately 3-4 min. in such climate control devices. Consequently, it is in particular not possible to remove a sample from the climate chamber, for example for the purpose preliminary analysis. However, removal would be desirable, for example for evaluating the cell growth over a specific period, since in this case individual samples need not be incubated in separate incubators over different periods, but the entire incubation process can take place in one incubator.

The climate control device according to the invention comprises a channel or a compartment or a chamber through which flows the gaseous medium to be conditioned. Normally, said medium is air charged with gases, such as $CO_2$, if necessary. Further, the climate control device comprises a steam chamber having an inlet opening, and an outlet opening which is connected with the channel. In the steam chamber, which is connected with a steam generation means, such as a spraying or a heating device, steam, for example water vapor, is produced. If a spraying device is used as a steam generation means, an aerosol, i.e. finely distributed liquid drops, is produced in a gaseous medium. Heating causes evaporation of a liquid. Evaporation of a liquid bath by heating already includes the evaporation enthalpy, whereas in the case of spraying said enthalpy has to be added via a heating means.

According to the invention, a control means for controlling the quantity of steam transported from the steam chamber to the channel is arranged at the inlet opening and/or the outlet opening of the steam chamber. According to the invention, the steam or an aerosol is thus not directly introduced into the medium to be conditioned, but first stored in a steam chamber. It is thus possible to produce a supply of steam in the steam chamber, which can be fed to the medium to be conditioned within a short period of time. If the control means fully opens the inlet and/or the outlet opening of the steam chamber such that a maximum steam volume flow is fed from the steam chamber to the channel, the climate control device according to the invention allows an air moisture of more than 80%, in particular more than 90%, and more preferably more than 95% to be reached in less than five minutes, in particular in less than three minutes. This value can be reached in a volume flow of the gaseous medium of approximately 40-50 liters/sec., a climate chamber volume of 50-80 liters and a volume of the steam chamber of approximately 1 liter.

Preferably, the steam generation means is a heating device with the aid of which a high air moisture is produced by evaporation of water or a fluid. This offers the advantage, as compared with a spraying means which produces an aerosol, that steam does not so easily condense out or precipitate on surfaces as an aerosol.

With the aid of the control means according to the invention the opening cross section of the inlet and/or the outlet opening of the steam chamber can preferably be varied. This is preferably realized with a displaceable cover element such that the opening cross section can be quickly varied in a simple manner. Preferably, the cover element is a proportional gate. If the climate control device according to the invention is in particular to be used for climate control in incubators for chemical and/or biological samples, the inlet opening of the steam chamber is preferably connected with the channel. This offers the advantage that no foreign air, which may contain impurities, can be fed through the inlet openings into the system.

Further, the displaceable cover element may be a cylindrical element which is displaceable relative to a slot-shaped outlet opening. The cylindrical element is arranged in correspondingly annular bearings such that it is adapted to be smoothly displaced.

It is further possible to provide a flap at the opening such that the size of the outlet area can be varied by the flap position. The flap is preferably configured such that the opening angle of the flap is directly proportional to the cross sectional area. This considerably facilitates the control operation.

Preferably, the climate control device comprises a filter means which filters out the impurities, bacteria etc. contained in the medium to be conditioned. Preferably, the filter means is arranged upstream of the steam chamber, in particular upstream of the outlet opening of the steam chamber. The medium is thus filtered prior to renewed or additional charging with steam.

Further, the climate control device according to the invention may comprise a conditioning means for heating and/or cooling the conditioned medium. The conditioning means is preferably arranged downstream of the steam chamber such that medium freshly charged with steam subsequently flows through the conditioning means. Provision of a conditioning means which can also be used for cooling purposes, if necessary, offers the advantage that the medium temperature, which has been increased by the introduction of steam, can be decreased again if such a temperature increase is undesired. It is thus possible to control the moisture content of the medium within large ranges independent of the medium temperature. The range is substantially limited by physical limitations, i.e. in particular the ability of the medium to absorb moisture as a function of the temperature (dew point). Tests have shown that the fluid, which is present in the steam chamber for evaporation purposes, is preferably adjusted to a temperature of 40-65° since otherwise too large an influence is exerted on the temperature of the medium to be conditioned, and extensive cooling would be necessary. The cooling process further allows the temperature to be kept below 30° at a high moisture of preferably 90%.

Preferably, the steam chamber contains a liquid which is evaporated by the heating means. For keeping the liquid quantity within a specific predetermined range, the steam chamber is preferably connected with a liquid supply means. The liquid supply means may comprise an automatic filling-level meter, if necessary, such that liquid is automatically replenished.

The climate chamber according to the invention, which is preferably connected with the climate device described above, is in particular suitable for skin cultivation. When skin is cultivated in the climate chamber according to the invention, it is possible to carry out observations and/or analyses during the cultivation process with the aid of the microscope arranged in the chamber. Further, skin cultivation or cultivation of other cells may take place in a climate chamber connected with the climate control device according to the invention, wherein the climate chamber does not comprise a microscope or the like.

BRIEF DESCRIPTION OF THE DRAWINGS

A preferred embodiment of the invention will now be described in greater detail with reference to the drawings in which.

DETAILED DESCRIPTION OF THE PREFERRED EMBODIMENT

Figure 1:
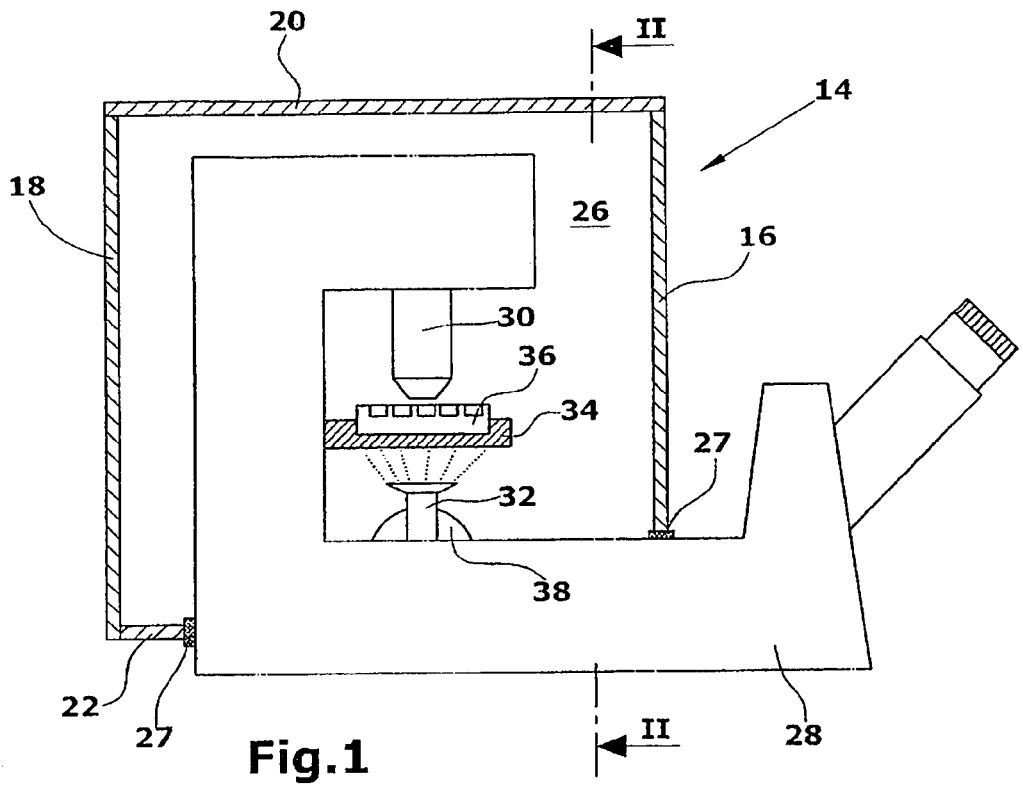
FIG. 1 shows a schematic partially sectional side view of the climate chamber placed upon a microscope.

A climate chamber comprises a plurality of side walls 12,14 (FIG. 2), a front wall 16 (FIG. 1), a rear wall 18, a top wall 20 and a bottom wall 22. The walls 12-22 form a housing 24 which defines a climate compartment 26. The housing 24 comprises a bottom wall 22 and a recess in the front wall 16 such that the housing 24 can be placed upon a microscope 28. The front wall 16 and the bottom wall 22 comprise sealing elements 27 which bear against the analysis device or the microscope 28 and substantially tightly seal the climate compartment 26 towards the outside. Essential components of the analysis device, which in the illustrated embodiment is a microscope 28, are thus arranged inside the climate compartment 26. These components are in particular an optical means 30 normally comprising a plurality of lenses, and an illumination means 32. Further, a sample table 34, which is normally of displaceable configuration, and a sample carrier 36, which is in particular a microtiter plate and is arranged on the sample table 34, are disposed inside the climate compartment 26.

For producing a uniform climate over a longer period of several hours or even several days in the climate compartment 26, the side wall 14 comprises an inlet opening 38 connected with a flexible tube 40 or any other supply means for supplying a medium flow 42. The medium flow 42 preferably is an air flow, wherein in particular the moisture, the temperature and, if necessary, the gas content of individual gases contained in the medium flow are adjusted with the aid of the air of an external climate control means. The medium flow 42 is directed such that it flows sideways below the sample carrier 36 (FIG. 2) when the sample carrier 36 is horizontally arranged. A preferred approach flow angle α relative to the sample carrier 36 is 30°-60°. The medium flow 42 not only flows against the sample carrier 36 but also against the optical means 30 and the illumination means 32. In particular, the medium flow 42 flows against a lower side 44 of the sample carrier 36 such that the chemical and/or biological sample arranged in the sample carrier can be well conditioned.

For allowing the temperature near the sample carrier 36 and thus the approximate temperature of the sample itself to be easily measured, a temperature sensor 46 is arranged below the sample carrier 36.

Further, the housing 24 comprises an outlet opening 48 in the rear wall 18. The outlet opening 48 is also connected with a flexible tube or the like and returns the medium flow to a climate control means such that medium flow circulation is ensured. The outlet opening 48 is arranged substantially opposite the inlet opening 38 to ensure as uniform a flow through the climate compartment 26 as possible. Further, the housing 24 is configured such that it promotes an optimum flow, wherein the embodiment shown in the drawings is a simplified representation. In particular adjacent side walls are preferably arranged at an angle of at least 90°, in particular at least 120°, relative to each other. For preventing, for example, "dead nooks", an additional wall extending inside the climate compartment 26 from the rear wall 18 to the top wall 20, as shown in FIG. 1, may be inserted between the rear wall 18 and the top wall 20. Thereby angles of more than 90° are realized between the rear wall 18 and the inserted wall as well as between the top wall 20 and the inserted wall. Further, the nooks can be provided with a radius to prevent formation of condensate in such nooks.

Preferably, the housing 24 comprises a door for allowing the sample carrier 36 to be exchanged in a simple manner. The door may, for example, be provided in the front wall 16 and may in particular be closable.

The climate chamber according to the invention is in particular suitable for confocal microscopes, wherein said microscopes may be imaging or nonimaging microscopes.

An imaging, in particular confocal, microscope preferably comprises a CCD array or the like, preferably for taking the picture of a sample.

The climate control device according to the invention comprises a channel 110 through which a gaseous medium, which is to be conditioned, flows in the direction indicated by arrow 112. For this purpose, the medium to be conditioned is sucked into the channel 110 with the aid of a fan 114 via a filter 116 which serves for removing particles, bacteria, etc. from the gaseous medium. When the medium has flown through the filter 116 and the channel 110, the medium is transported by the flow-producing means or the fan 114 through a conditioning means 118 which is a heating and/or cooling means. The medium thus flows through the climate control device in the direction of flow indicated by arrows 112.

Below the channel 110 a steam chamber 120 is provided. The steam chamber 120 is arranged, together with the channel 110, inside a common housing 122. A partition wall 124 thus divides the interior of the housing 122 into the channel 110 and the steam chamber 120. The steam chamber 120 is connected with a heating element 126 which serves for heat generation. The heating element 126 heats a lower side 128 of the housing 122. Thereby the water 130 in the steam chamber or any other liquid is heated such that steam 132 is generated above the liquid 130. The steam chamber 120 comprises an inlet opening 134 which, in the illustrated embodiment, is connected with the channel 110. The inlet opening 134 is arranged in the partition wall 124. In addition to or instead of the inlet opening 134 another inlet opening may be provided in a cover 136 of the housing 122. This other inlet opening is arranged in the region below the filter 116 in the side wall 136 laterally beside the partition wall 124. For this purpose, the partition wall 124, as shown in the Figure, does not extend continuously in parallel to the lower side 128 of the housing 122 but is bent on one side by approximately 90° and is connected with the side wall 136.

Further, the steam chamber 120 comprises an outlet opening 138 connected with the channel 110. Through the outlet opening 138 steam 132 is fed into the channel 110 to increase the air moisture of the medium transported through the climate control device.

In the illustrated embodiment, a control means 140 in the form of a gate or a cover element is provided near the outlet opening 138. The gate or the cover element 140 comprises an opening whose dimensions normally correspond to those of the outlet opening 138. The gate 140 is displaceable in the direction indicated by arrow 142. This allows the outlet opening 138 and the opening of the gate 140 to completely overlap each other when the control means is in its maximum open position. For controlling the quantity of steam flowing through the outlet opening 138 into the channel 110, the gate 140 can be displaced in the direction indicated by arrow 142 such that only a portion of the outlet opening 138 is open. By displacing the gate 140 in the direction indicated by the arrow, the opening cross section of the outlet opening 138 can thus be varied.

For keeping the liquid level of the liquid 130 constant for a long period, a filling level meter may be provided in the steam chamber 120, and the steam chamber 120 may be connected with a storage tank.

Further, it is possible to introduce gases, for example $CO_2$, via supply nozzles, inlets or the like into the medium flow.

Instead of the gate 140 (FIG. 3) a flap 150 (FIG. 4) may be provided for controlling the opening cross section of the outlet opening 138. The flap 150 is pivotable about an axis 152, wherein, depending on the opening angle of the flap 150, a different quantity of steam from the steam chamber 120 can flow into the chamber 110. Preferably, the flap 150 comprises a flap edge 154 pointing towards the opening 138, said flap edge 154 being configured as a web and having an outer contour matched to that of the flap. Selection or configuration of the outer contour allows a proportionality between the opening angle of the flap 150 and the thus opened outlet cross section of the outlet opening 138 to be realized in order to facilitate the control process.

Figure 2:
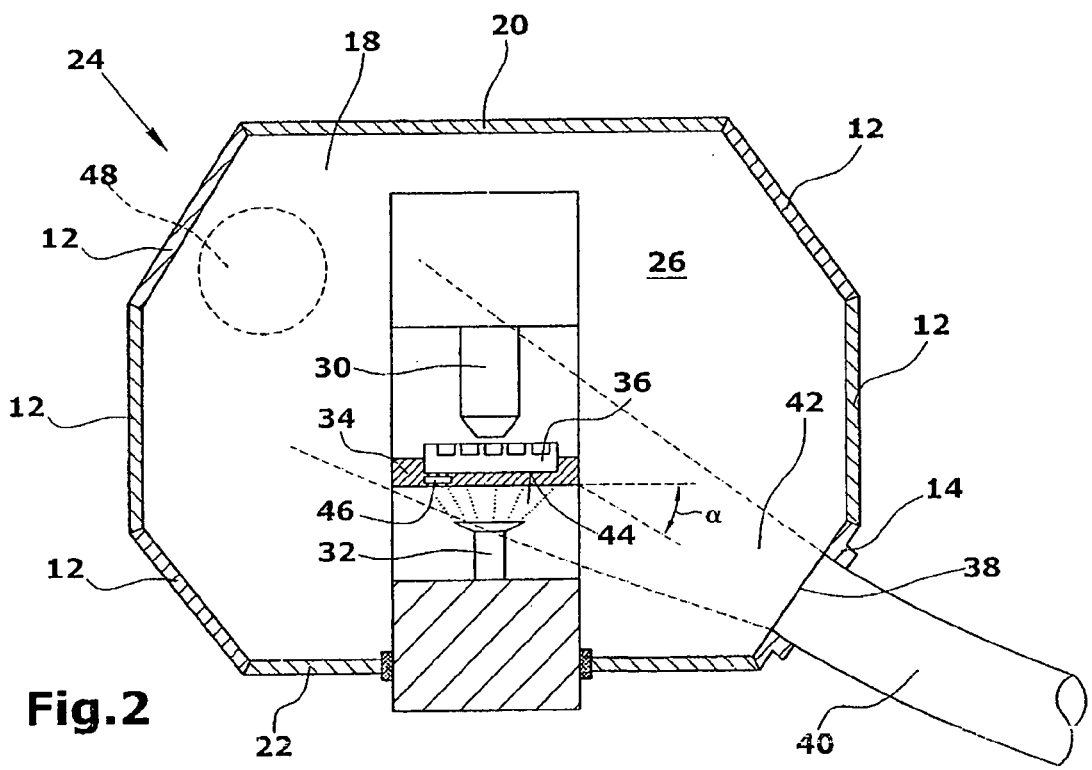
FIG. 2 shows a schematic partially sectional view along line II-II of FIG. 1.
Figure 3:
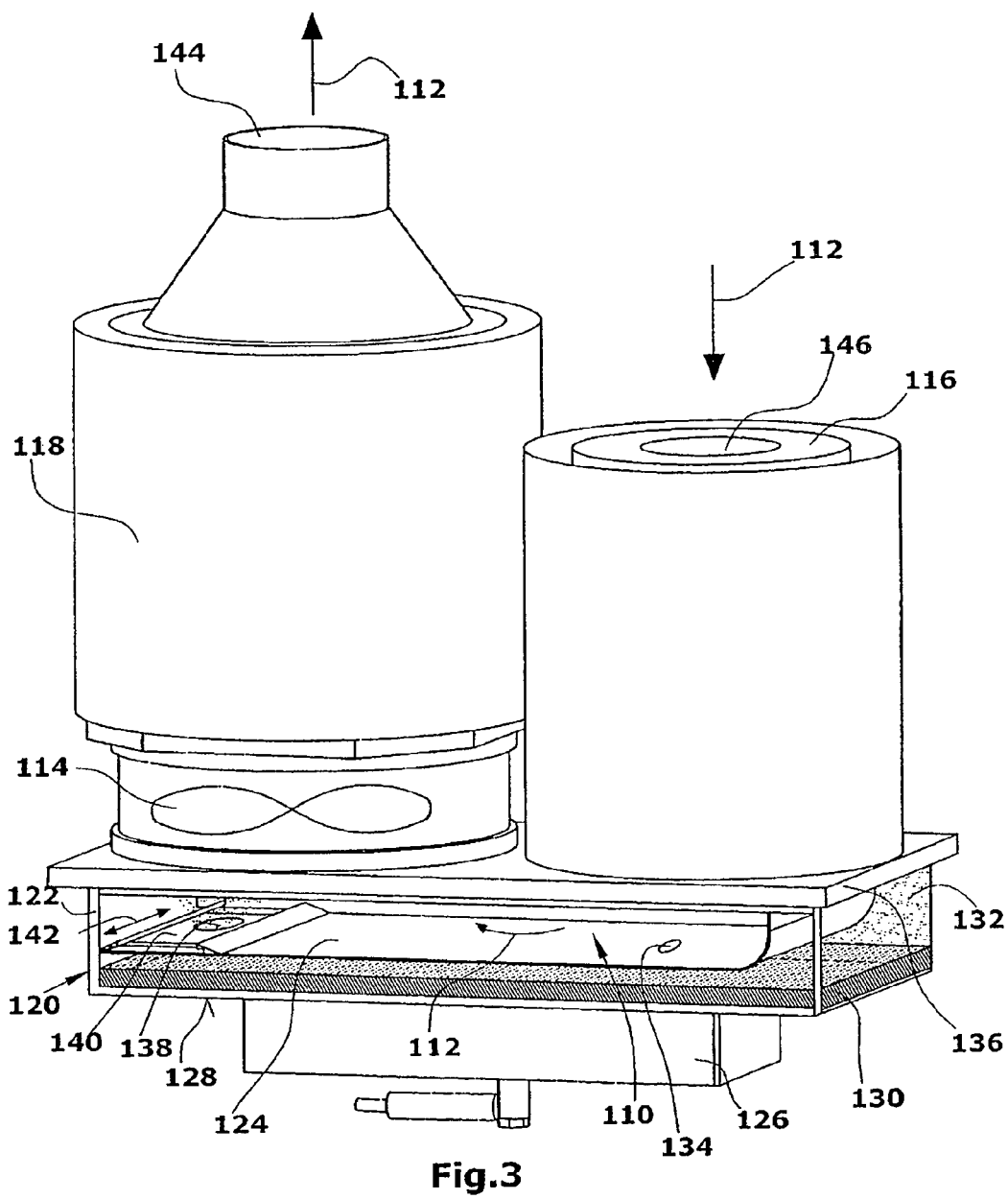
FIG. 3 shows a schematic perspective partially sectional view of a climate control device.
Figure 4:
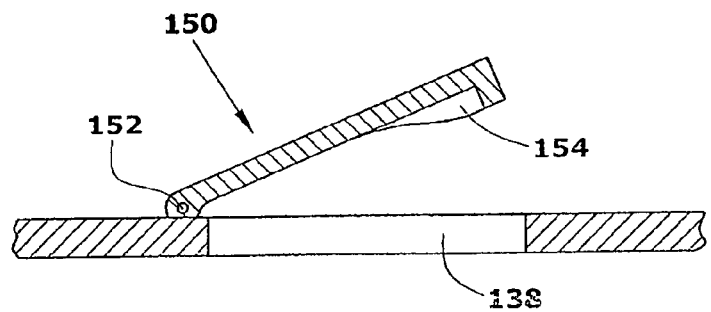
FIG. 4 shows a schematic sectional side view of another embodiment of a control means to be provided in the climate control device.

In a particular preferred embodiment, the climate chamber described with reference to FIGS. 1 and 2 is connected with a climate control device described with reference to FIGS. 3 and 4. For this purpose, an outlet 144 (FIG. 3) may be connected with the flexible tube 40 (FIG. 2). A flexible tube provided at the outlet opening 48 (FIG. 2) may be connected with the inlet 146 of the filter 116 (FIG. 3). The two device elements are thus connected only via two flexible tubes and may be arranged in spaced relationship to each other. This modular concept allows the individual device components to be connected with each other in different configurations. Further, the arrangement can be advantageously used in a laboratory such that, for example, the climate control device (FIG. 3) need not be arranged in the vicinity of the climate chamber where it may interfere with the climate chamber.

Further, the device according to the invention comprises a control device. This device may communicate or be connected with various sensors, actuators and the like. With the aid of the control device and the means connected therewith, for example sensors, the medium can be adjusted. In particular, the moisture content, the temperature, the $CO_2$ content, the content of other gases etc. are adjusted. Further, corresponding actuators may vary the approach flow angle of the medium 42 (FIG. 2). This can be realized by using redirecting elements, such as guide plates, which may of course be made of plastic material, or by varying the position of the flexible tube 40 or the inlet opening 38.

The invention claimed is:

1. A climate chamber comprising:
    a housing defining a climate compartment,
    an analysis device arranged at least partially in the climate compartment for analyzing a sample,
    an inlet opening provided in the housing for supplying a conditioning medium flow, and
    a directing device for directing the conditioning medium flow,
    wherein the directing device is configured to direct the conditioning medium flow to flow at least partially against a sample carrier arranged in the climate compartment.

2. The climate chamber according to claim 1, wherein said medium flow is directed such that the medium flow flows against a lower side of the sample carrier.

3. The climate chamber according to claim 1, wherein said inlet opening is arranged laterally offset below the sample carrier when the sample carrier is horizontally arranged.

4. The climate chamber according to claim 1, further comprising an approach flow angle ($\alpha$) of 30°-60° relative to the sample carrier.

5. The climate chamber according to claim 1, wherein said medium flow is directed such that at least 50%-70% of the medium flow flows against the analysis device and/or the sample carrier.

6. The climate chamber according to claim 1, further comprising condensate-sensitive components of the analysis device being located in the medium flow.

7. The climate chamber according to claim 1, further comprising a temperature sensor arranged near the sample carrier.

8. The climate chamber according to claim 1, further comprising an outlet opening provided in the housing, wherein said outlet opening being arranged substantially opposite the inlet opening.

9. The climate chamber according to claim 1, wherein the housing is configured such that it promotes an optimum flow.

10. The climate chamber according to claim 1, further comprising adjacent housing walls arranged at an angle of at least 90° relative to each other.

11. The climate chamber according to claim 1 having a climate control system comprising a climate chamber, said climate chamber comprising a housing defining a climate compartment, an analysis device arranged at least partially in the climate compartment for analyzing the sample, and an inlet opening provided in the housing for supplying a conditioning medium flow, wherein the medium flow flows at least partially against the analysis device and/or a sample carrier arranged in the climate compartment, wherein the inlet opening has connected therewith a climate control device; a channel through which flows a gaseous medium which is to be conditioned; a steam chamber having an inlet opening and an outlet opening connected with said channel; a steam generator connected with said steam chamber; and a controller arranged at the inlet opening and/or the outlet opening for controlling the quantity of steam fed from the steam chamber to the channel.

12. The climate control system according to claim 11, wherein said controller is adapted to control the opening cross section of the inlet opening and/or the outlet opening.

13. The climate control system according to claim 11, wherein the inlet opening is connected with the channel such that a portion of the medium to be conditioned flows into the steam chamber.

14. The climate control system according to claim 11, wherein the steam generator comprises a heater for heating the medium to be evaporated.

15. The climate control system according to claim 11, further comprising a flow-producer for producing the medium flow in the channel.

16. The climate control system according to claim 11, further comprising a filter connected with the channel.

17. The climate control system according to claim 11, further comprising a conditioner connected with the channel.

18. A climate chamber comprising:

a climate compartment defined by a front wall, a rear wall, a top wall, a bottom wall, a first plurality of side walls, and a second plurality of side walls, an analysis device arranged at least partially in the climate compartment for analyzing a sample disposed in a sample carrier, the analysis device having an optical device and an illumination device, and an inlet opening defined in one of the first plurality of side walls, the inlet opening being configured to supply a conditioning medium flow against the optical device, the illumination device, and a lower side of the sample carrier at a flow approach angle relative to the horizontal between 30° and 60°.

19. The climate chamber according to claim 18, wherein the first plurality of side walls are at an angle of more than 90° relative to each other and the first plurality of side walls are at an angle of more than 90° relative to each other.

* * * * *